US010974027B2

(12) United States Patent
McNiven et al.

(10) Patent No.: US 10,974,027 B2
(45) Date of Patent: Apr. 13, 2021

(54) COMBINATION STEERABLE CATHETER AND SYSTEMS

(71) Applicant: Cephea Valve Technologies, Inc., Santa Clara, CA (US)

(72) Inventors: Sean A. McNiven, Menlo Park, CA (US); Fransisco Valencia, East Palo Alto, CA (US); Randolf von Oepen, Aptos, CA (US)

(73) Assignee: CEPHEA VALVE TECHNOLOGIES, INC., Santa Clara, CA (US)

( * ) Notice: Subject to any disclaimer, the term of this patent is extended or adjusted under 35 U.S.C. 154(b) by 0 days.

(21) Appl. No.: 15/662,013

(22) Filed: Jul. 27, 2017

(65) Prior Publication Data
US 2018/0028787 A1 Feb. 1, 2018

Related U.S. Application Data

(60) Provisional application No. 62/368,702, filed on Jul. 29, 2016.

(51) Int. Cl.
*A61M 25/01* (2006.01)
*A61F 2/24* (2006.01)
(Continued)

(52) U.S. Cl.
CPC .......... *A61M 25/0147* (2013.01); *A61B 5/01* (2013.01); *A61B 5/0215* (2013.01);
(Continued)

(58) Field of Classification Search
CPC .......... A61M 25/0147; A61M 25/0026; A61M 25/0136; A61B 5/01; A61B 5/0215; A61B 5/6852; A61F 2/24; A61F 2/2427
(Continued)

(56) References Cited

U.S. PATENT DOCUMENTS

| 4,406,656 A | 9/1983 | Hattler et al. |
| 4,728,319 A | 3/1988 | Masch |

(Continued)

FOREIGN PATENT DOCUMENTS

| CN | 1469724 | 1/2004 |
| CN | 1688352 A | 10/2005 |

(Continued)

OTHER PUBLICATIONS

Takizawa H et al: "Development of a microfine active bending catheter equipped with MIF tactile sensors", Micro Electro Mechanical Systems, 1999. MEMS '99. Twelfth IEEE International Conference on Orlando, FL, USA Jan. 17-21, 1999, Piscataway, NJ, USA, IEEE, US, Jan. 17, 1999 (Jan. 17, 1999), pp. 412-417, XP010321677, ISBN: 978-0-7803-5194-3 figures 1-3.

(Continued)

*Primary Examiner* — Daniel L Cerioni
(74) *Attorney, Agent, or Firm* — Workman Nydegger

(57) ABSTRACT

A steerable catheter has a body with an outer surface and an inner surface defining a central lumen. The outer surface and inner surface define a wall of the body, which has a plurality of steering lumen and control lumen extending longitudinally therethrough. The body includes a body material. The steering lumen and control lumen have a control lumen lining and steering lumen lining, respectively, with a higher durometer than the body material. A steering wire is positioned within the steering lumen and a control wire is positioned within the control lumen.

8 Claims, 7 Drawing Sheets

(51) Int. Cl.
*A61B 5/01* (2006.01)
*A61B 5/0215* (2006.01)
*A61B 5/00* (2006.01)
*A61M 25/00* (2006.01)

(52) U.S. Cl.
CPC .............. *A61B 5/6852* (2013.01); *A61F 2/24* (2013.01); *A61F 2/2427* (2013.01); *A61M 25/0026* (2013.01); *A61M 25/0136* (2013.01); *A61F 2/2466* (2013.01); *A61M 25/0045* (2013.01); *A61M 2025/004* (2013.01); *A61M 2025/0046* (2013.01); *A61M 2025/0047* (2013.01); *A61M 2205/332* (2013.01); *A61M 2205/3334* (2013.01)

(58) Field of Classification Search
USPC ........................................................ 600/585
See application file for complete search history.

(56) References Cited

U.S. PATENT DOCUMENTS

| | | |
|---|---|---|
| 5,053,043 A | 10/1991 | Gottesman et al. |
| 5,059,213 A | 10/1991 | Chesterfield et al. |
| 5,078,722 A | 1/1992 | Stevens |
| 5,078,723 A | 1/1992 | Dance et al. |
| 5,236,450 A | 8/1993 | Scott |
| 5,325,845 A | 7/1994 | Adair |
| 5,345,945 A | 9/1994 | Hodgson et al. |
| 5,387,219 A | 2/1995 | Rappe |
| 5,415,664 A | 5/1995 | Pinchuk |
| 5,472,423 A | 12/1995 | Gronauer |
| 5,472,426 A | 12/1995 | Gronauer |
| 5,571,085 A | 11/1996 | Accisano, III |
| 5,662,606 A | 9/1997 | Cimino et al. |
| 5,669,919 A | 9/1997 | Sanders et al. |
| 5,769,812 A | 6/1998 | Stevens et al. |
| 5,807,405 A | 9/1998 | Vanney et al. |
| 5,820,591 A | 10/1998 | Thompson et al. |
| 5,843,103 A | 12/1998 | Wulfman |
| 5,855,601 A | 1/1999 | Bessler et al. |
| 5,873,882 A | 2/1999 | Straub et al. |
| 5,902,334 A | 5/1999 | Dwyer et al. |
| 5,906,642 A | 5/1999 | Caudillo et al. |
| 5,957,973 A | 9/1999 | Quiachon et al. |
| 6,090,118 A | 7/2000 | McGuckin, Jr. |
| 6,180,059 B1 | 1/2001 | Divino, Jr. et al. |
| 6,228,110 B1 | 5/2001 | Munsinger |
| 6,458,137 B1 | 10/2002 | Klint |
| 6,517,550 B1 | 2/2003 | Konya et al. |
| 6,695,836 B1 | 2/2004 | DeMello et al. |
| 6,926,725 B2 | 8/2005 | Cooke et al. |
| 7,172,617 B2 | 2/2007 | Colgan et al. |
| 7,344,553 B2 | 3/2008 | Opolski et al. |
| 7,666,204 B2 | 2/2010 | Thornton et al. |
| 7,736,388 B2 | 6/2010 | Goldfarb et al. |
| 7,837,727 B2 | 11/2010 | Goetz et al. |
| 7,988,724 B2 | 8/2011 | Salahieh et al. |
| 7,993,303 B2 | 8/2011 | Von Oepen et al. |
| 8,157,852 B2 | 4/2012 | Bloom et al. |
| 8,523,881 B2 | 9/2013 | Cabiri et al. |
| 8,647,323 B2 | 2/2014 | Guo et al. |
| 8,911,455 B2 | 12/2014 | Quadri et al. |
| 8,926,588 B2 | 1/2015 | Berthiaume et al. |
| 8,926,692 B2 | 1/2015 | Dwork |
| 9,339,378 B2 | 5/2016 | Quadri et al. |
| 9,370,423 B2 | 6/2016 | Ryan |
| 9,393,112 B2 | 7/2016 | Tuval et al. |
| 9,399,112 B2 | 7/2016 | Shevgoor et al. |
| 9,668,859 B2 | 6/2017 | Kheradvar et al. |
| 9,687,373 B2 | 6/2017 | Vad |
| 9,693,862 B2 | 7/2017 | Campbell et al. |
| 9,801,745 B2 | 10/2017 | Wubbeling et al. |
| 10,111,671 B2 | 10/2018 | Bodewadt |
| 10,117,760 B2 | 11/2018 | Mangiardi |
| 10,376,673 B2 | 8/2019 | Van Hoven et al. |
| 10,398,553 B2 | 9/2019 | Kizuka |
| 10,470,902 B2 | 11/2019 | Sheldon et al. |
| 2001/0002445 A1 | 5/2001 | Vesely |
| 2001/0047150 A1 | 11/2001 | Chobotov |
| 2002/0013547 A1 | 1/2002 | Paskar |
| 2004/0049207 A1 | 3/2004 | Goldfarb et al. |
| 2004/0064179 A1 | 4/2004 | Linder et al. |
| 2004/0116848 A1* | 6/2004 | Gardeski ............ A61M 25/0147 604/95.01 |
| 2004/0127849 A1 | 7/2004 | Kantor |
| 2004/0133232 A1 | 7/2004 | Rosenbluth et al. |
| 2004/0147826 A1 | 7/2004 | Peterson |
| 2005/0038383 A1 | 2/2005 | Kelley et al. |
| 2005/0085903 A1 | 4/2005 | Lau |
| 2005/0137695 A1 | 6/2005 | Salahieh et al. |
| 2005/0143809 A1* | 6/2005 | Salahieh ............... A61F 2/2418 623/2.11 |
| 2005/0256452 A1 | 11/2005 | DeMarchi et al. |
| 2005/0259452 A1 | 11/2005 | DeMarchi et al. |
| 2005/0283231 A1 | 11/2005 | Haug et al. |
| 2005/0277874 A1* | 12/2005 | Selkee ............... A61M 25/0136 604/95.04 |
| 2005/0277876 A1 | 12/2005 | Hayden |
| 2005/0288768 A1 | 12/2005 | Sowinski et al. |
| 2006/0135961 A1 | 6/2006 | Rosenman et al. |
| 2007/0060997 A1 | 3/2007 | de Boer |
| 2007/0156225 A1 | 7/2007 | George et al. |
| 2007/0173757 A1 | 7/2007 | Levine et al. |
| 2007/0197858 A1 | 8/2007 | Goldfarb et al. |
| 2007/0203561 A1 | 8/2007 | Forster et al. |
| 2007/0260225 A1 | 11/2007 | Sakakine et al. |
| 2007/0270779 A1 | 11/2007 | Jacobs et al. |
| 2007/0299424 A1 | 12/2007 | Cumming et al. |
| 2008/0103585 A1 | 5/2008 | Monstadt et al. |
| 2008/0109065 A1 | 5/2008 | Bowe |
| 2008/0188850 A1 | 8/2008 | Mody et al. |
| 2008/0195126 A1 | 8/2008 | Solem |
| 2009/0036768 A1 | 2/2009 | Seehusen et al. |
| 2009/0069885 A1 | 3/2009 | Randert et al. |
| 2009/0099554 A1 | 4/2009 | Forster et al. |
| 2009/0163934 A1 | 6/2009 | Raschdorf, Jr. et al. |
| 2009/0182407 A1 | 7/2009 | Leanna et al. |
| 2009/0204005 A1 | 8/2009 | Keast et al. |
| 2009/0240326 A1 | 9/2009 | Wilson et al. |
| 2009/0276039 A1 | 11/2009 | Meretei |
| 2009/0281619 A1 | 11/2009 | Le et al. |
| 2010/0004739 A1 | 1/2010 | Vesely |
| 2010/0044410 A1 | 2/2010 | Argentine et al. |
| 2010/0059173 A1 | 3/2010 | Kampa et al. |
| 2010/0070009 A1 | 3/2010 | Barker |
| 2010/0217261 A1 | 8/2010 | Watson |
| 2010/0249894 A1 | 9/2010 | Oba et al. |
| 2010/0331776 A1 | 12/2010 | Salahieh et al. |
| 2011/0112630 A1 | 5/2011 | Groothuis et al. |
| 2011/0166566 A1 | 7/2011 | Gabriel |
| 2011/0166649 A1* | 7/2011 | Gross ................... A61F 2/2445 623/2.36 |
| 2011/0202128 A1 | 8/2011 | Duffy |
| 2011/0257718 A1 | 10/2011 | Argentine |
| 2011/0307049 A1 | 12/2011 | Kao |
| 2012/0022640 A1 | 1/2012 | Gross et al. |
| 2012/0065464 A1 | 3/2012 | Ellis et al. |
| 2012/0109078 A1 | 5/2012 | Schaeffer |
| 2012/0172915 A1 | 7/2012 | Fifer et al. |
| 2012/0316639 A1 | 12/2012 | Kleinschrodt |
| 2012/0330348 A1 | 12/2012 | Strauss et al. |
| 2012/0330408 A1 | 12/2012 | Hillukka et al. |
| 2013/0030514 A1 | 1/2013 | Kasprzak et al. |
| 2013/0041314 A1 | 2/2013 | Dillon |
| 2013/0066342 A1 | 3/2013 | Dell et al. |
| 2013/0103001 A1 | 4/2013 | BenMaamer et al. |
| 2013/0109910 A1 | 5/2013 | Alexander et al. |
| 2013/0131775 A1 | 5/2013 | Hadley et al. |
| 2013/0289696 A1 | 10/2013 | Maggard et al. |
| 2014/0107693 A1 | 4/2014 | Plassman |
| 2014/0114390 A1 | 4/2014 | Tobis et al. |
| 2014/0142688 A1 | 5/2014 | Duffy et al. |
| 2014/0148889 A1 | 5/2014 | Deshmukh et al. |

(56) References Cited

U.S. PATENT DOCUMENTS

| | | | |
|---|---|---|---|
| 2014/0180124 A1* | 6/2014 | Whiseant | A61B 5/02055 600/467 |
| 2014/0200649 A1 | 7/2014 | Essinger et al. | |
| 2014/0228871 A1 | 8/2014 | Cohen et al. | |
| 2014/0276966 A1 | 9/2014 | Ranucci et al. | |
| 2014/0324164 A1 | 10/2014 | Gross et al. | |
| 2014/0336744 A1 | 11/2014 | Tani et al. | |
| 2014/0379074 A1 | 12/2014 | Spence et al. | |
| 2015/0005704 A1 | 1/2015 | Heisel et al. | |
| 2015/0005801 A1 | 1/2015 | Marquis et al. | |
| 2015/0088189 A1 | 3/2015 | Paul, Jr. | |
| 2015/0112430 A1 | 4/2015 | Creaven et al. | |
| 2015/0272759 A1 | 10/2015 | Argentine | |
| 2015/0306806 A1* | 10/2015 | Dando | A61M 25/0009 264/515 |
| 2016/0045311 A1 | 2/2016 | McCann et al. | |
| 2016/0074163 A1 | 3/2016 | Yang et al. | |
| 2016/0113765 A1 | 4/2016 | Ganesan et al. | |
| 2016/0143661 A1 | 5/2016 | Wood et al. | |
| 2017/0035566 A1* | 2/2017 | Krone | A61F 2/2427 |
| 2017/0042678 A1 | 2/2017 | Ganesan et al. | |
| 2017/0080186 A1 | 3/2017 | Salahieh et al. | |
| 2017/0232238 A1* | 8/2017 | Biller | A61M 1/3666 604/509 |
| 2018/0028177 A1 | 2/2018 | von Oepen et al. | |
| 2018/0028215 A1 | 2/2018 | Cohen | |
| 2018/0028305 A1 | 2/2018 | von Oepen et al. | |
| 2018/0028779 A1 | 2/2018 | von Oepen et al. | |
| 2018/0055636 A1 | 3/2018 | Valencia et al. | |
| 2018/0055637 A1 | 3/2018 | von Oepen et al. | |
| 2018/0056033 A1 | 3/2018 | von Oepen et al. | |
| 2018/0056043 A1 | 3/2018 | von Oepen et al. | |
| 2018/0071098 A1 | 3/2018 | Alon | |
| 2018/0092744 A1 | 4/2018 | von Oepen et al. | |
| 2018/0126119 A1 | 5/2018 | McNiven et al. | |
| 2018/0132837 A1 | 5/2018 | Mathena et al. | |
| 2018/0133454 A1 | 5/2018 | von Oepen et al. | |
| 2018/0360457 A1 | 12/2018 | Ellis et al. | |
| 2019/0030285 A1 | 1/2019 | Prabhu et al. | |
| 2019/0274831 A1 | 9/2019 | Prabhu | |
| 2020/0155804 A1 | 5/2020 | Von et al. | |
| 2020/0230352 A1 | 7/2020 | Mcniven et al. | |
| 2020/0230354 A1 | 7/2020 | Von Oepen et al. | |

FOREIGN PATENT DOCUMENTS

| | | |
|---|---|---|
| CN | 1961983 A | 5/2007 |
| CN | 101247847 A | 8/2008 |
| CN | 101426452 A | 5/2009 |
| CN | 101506538 A | 8/2009 |
| CN | 102159277 A | 8/2011 |
| CN | 102258402 A | 11/2011 |
| CN | 102481433 A | 5/2012 |
| CN | 102548505 A | 7/2012 |
| CN | 102770080 | 11/2012 |
| CN | 102933161 A | 2/2013 |
| CN | 103517689 A | 1/2014 |
| CN | 103702635 A | 4/2014 |
| CN | 103841899 | 6/2014 |
| CN | 103957993 A | 7/2014 |
| CN | 104203329 A | 12/2014 |
| CN | 104812439 A | 7/2015 |
| CN | 105246434 A | 1/2016 |
| CN | 105899167 A | 8/2016 |
| EP | 1980288 | 4/2008 |
| EP | 1980288 | 10/2008 |
| EP | 2537487 | 12/2012 |
| EP | 2702965 | 3/2014 |
| EP | 3009103 | 4/2016 |
| JP | 2003062072 | 3/2003 |
| JP | 2006528911 | 12/2006 |
| JP | 2013516244 | 5/2013 |
| WO | WO 2001051114 | 7/2001 |
| WO | WO 2007044285 | 4/2007 |
| WO | WO 2007136829 | 11/2007 |
| WO | WO 2008103722 | 8/2008 |
| WO | WO 2010024801 | 3/2010 |
| WO | WO 2010121076 | 10/2010 |
| WO | WO 2012020521 | 2/2012 |
| WO | 2012/057983 A1 | 5/2012 |
| WO | WO 2012151396 | 11/2012 |
| WO | 2013/126529 A2 | 8/2013 |
| WO | WO 2014064694 | 5/2014 |
| WO | WO 2014121280 | 8/2014 |
| WO | WO 2014128705 | 8/2014 |
| WO | WO 2015191938 | 12/2015 |
| WO | WO 2016022797 | 2/2016 |
| WO | WO 2016112085 | 7/2016 |
| WO | WO 2016144708 | 9/2016 |
| WO | WO 2016150806 | 9/2016 |
| WO | WO 2016183526 | 11/2016 |
| WO | 2017/023534 A2 | 2/2017 |
| WO | WO 2018023038 | 2/2018 |
| WO | WO 2018023043 | 2/2018 |
| WO | WO 2018023044 | 2/2018 |
| WO | WO 2018023045 | 2/2018 |
| WO | WO 2018023052 | 2/2018 |
| WO | WO 2018044446 | 3/2018 |
| WO | WO 2018044447 | 3/2018 |
| WO | WO 2018044448 | 3/2018 |
| WO | WO 2018044449 | 3/2018 |
| WO | WO 2018067788 | 4/2018 |
| WO | WO 2018093426 | 5/2018 |

OTHER PUBLICATIONS

U.S. Appl. No. 15/662,001, Mar. 24, 2020, Notice of Allowance.
U.S. Appl. No. 15/662,008, Jan. 31, 2020, Notice of Allowance.
U.S. Appl. No. 15/662,066, Feb. 27, 2020, Advisory Action.
U.S. Appl. No. 15/662,076, Jan. 31, 2020, Notice of Allowance.
U.S. Appl. No. 15/662,089, Jan. 10, 2020, Office Action.
U.S. Appl. No. 15/662,098, Jan. 27, 2020, Office Action.
U.S. Appl. No. 15/662,098, Mar. 23, 2020, Advisory Action.
U.S. Appl. No. 15/724,499, Mar. 25, 2020, Office Action.
U.S. Appl. No. 15/662,142, Apr. 17, 2020, Office Action.
U.S. Appl. No. 15/662,001, Jun. 20, 2019, Office Action.
U.S. Appl. No. 15/662,001, Oct. 4, 2019, Office Action.
U.S. Appl. No. 15/662,001, Dec. 18, 2019, Notice of Allowance.
U.S. Appl. No. 15/662,066, Jul. 11, 2019, Office Action.
U.S. Appl. No. 15/662,066, Dec. 16, 2019, Office Action.
U.S. Appl. No. 15/662,142, Dec. 20, 2019, Advisory Action.
U.S. Appl. No. 15/662,076, Oct. 8, 2019, Notice of Allowance.
U.S. Appl. No. 15/662,089, Oct. 7, 2019, Office Action.
U.S. Appl. No. 15/662,093, Mar. 7, 2019, Office Action.
U.S. Appl. No. 15/662,093, Aug. 29, 2019, Office Action.
U.S. Appl. No. 15/662,093, Dec. 3, 2019, Office Action.
U.S. Appl. No. 15/662,008, Sep. 13, 2019, Office Action.
U.S. Appl. No. 15/662,014, May 31, 2019, Office Action.
U.S. Appl. No. 15/662,014, Oct. 2, 2019, Notice of Allowance.
U.S. Appl. No. 15/662,098, Jul. 5, 2019, Office Action.
U.S. Appl. No. 15/724,499, Jul. 15, 2019, Notice of Allowance.
U.S. Appl. No. 15/724,499, Aug. 27, 2019, Notice of Allowance.
U.S. Appl. No. 15/724,499, Nov. 25, 2019, Notice of Allowance.
Hironobu Takizawa et al. "Development of a Microfine Active Bending Catheter Equipped with MIF Tactile Sensors", Micro Electro Mechanical Systems, IEEE, Jan. 17, 1999, pp. 412-417.
Advisory Action received for U.S. Appl. No. 15/662,093, dated Jul. 9, 2020.
Notice of Allowance received for U.S. Appl. No. 15/724,499, dated Jul. 1, 2020.
Office Action received for U.S. Appl. No. 15/662,066, dated May 21, 2020.
Office Action received for U.S. Appl. No. 15/662,089, dated Jun. 11, 2020.
Office Action received for U.S. Appl. No. 15/662,093, dated Aug. 29, 2019.
Office Action received for U.S. Appl. No. 15/662,093, dated May 6, 2020.

(56) References Cited

OTHER PUBLICATIONS

Office Action received for U.S. Appl. No. 15/662,098, dated Apr. 30, 2020.

* cited by examiner

COMBINATION STEERABLE CATHETER AND SYSTEMS

CROSS-REFERENCE TO RELATED APPLICATIONS

This application claims priority to U.S. Provisional Patent Application No. 62/368,702, filed Jul. 29, 2016, the entire contents of which are incorporated by reference herein.

BACKGROUND OF THE DISCLOSURE

Intravascular medical procedures allow the performance of therapeutic treatments in a variety of locations within a patient's body while requiring only relatively small access incisions. An intravascular procedure may, for example, eliminate the need for open-heart surgery, thereby reducing the risks, costs, and time associated with an open-heart procedure. The intravascular procedure also enables faster recovery times with lower associated costs and risks of complication. An example of an intravascular procedure which significantly reduces procedure and recovery time and cost over conventional open surgery is a heart valve replacement or repair procedure. An artificial valve is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more wires positioned inside the catheter. Precise control of the distal end of the catheter allows for more reliable and faster positioning of a medical device and/or implant and other improvements in the procedures.

The devices can also be directed through the valve chordae or papillary muscles, for example, for interventional therapy to the mitral valve. When such procedures require the use of more than one instrument, each instrument would be dependent upon proper positioning in relation to the valve. Therefore, positioning or steering mechanisms need to be built into each instrument. This adds further cost, complexity, and time to the procedures.

Other procedures may include tracking a catheter and/or access sheath from a puncture in the femoral vein through the intra-atrial septum to the left atrium. This pathway may be used to access the left atrium for ablation of the atrium wall or ablation around the pulmonary veins. Such interventional therapies would require precise alignment with target areas for proper ablation placement. Additionally, alternative access routes and/or access routes to other cavities may be desired.

To overcome some of these challenges, steerable catheter systems include one or more wires that allow manual flexion of the catheter system by an operator at a proximal end of the catheter system. The catheter system may thereby have a distal portion or other portion with an operator-adjustable curvature to allow navigation of the catheter system to the target location. A wire or wires in the catheter system, however, may shift in position within the catheter system. Further, torqueing the catheter system during navigation of the vasculature may cause changes in the position of contents in such catheter systems. Movements of the wires within the guide catheter or delivery catheter may compromise the precision with which the catheter may be oriented in the patient's body or the precision with which the operation and/or deployment of a medical device attached to the distal end thereof may be controlled.

Individual compartmentalization of the wires of the steering system increases the thickness of the catheter wall, and limits the utility of the central lumen. For example, a steerable catheter with one or more channels in the wall of the catheter for wires has a smaller inner diameter relative to the outer diameter than a catheter without channels in the wall. Many procedures utilize a plurality of steerable catheters, and the increased wall thickness compounds, increasing the necessary diameter of the delivery system.

BRIEF SUMMARY OF THE DISCLOSURE

In an embodiment, a multi-lumen catheter includes a body, a central lumen, at least one steering lumen, and at least one control lumen. The body has an outer surface and an inner surface defining a wall therebetween. The inner surface defines the central lumen, which extends in a longitudinal direction. The at least one steering lumen is defined by a steering lumen surface located in the wall. The steering lumen surface has a steering lumen lining, which defines a steering lumen diameter. The at least one control lumen is defined by a control lumen surface located in the wall. The control lumen surface has a control lumen lining, which defines a control lumen diameter.

In another embodiment, an intravascular device delivery system includes an elongated member, a steering wire, a control wire, and a handle. The elongate member includes a body, a central lumen, a steering lumen, and a control lumen. The body has an outer surface and an inner surface defining a wall therebetween. The inner surface defines the central lumen, which extends in a longitudinal direction. The steering lumen is defined by a steering lumen surface located in the wall. The steering lumen surface has a steering lumen lining, which defines a steering lumen diameter. The control lumen is defined by a control lumen surface located in the wall. The control lumen surface has a control lumen lining, which defines a control lumen diameter. The steering wire is located in the steering lumen and the control wire is located in the control lumen. The steering wire has a distal end piece located at a distal end of the steering wire and distally of the distal end of the steering lumen. The handle is connected to the proximal end of the body and operably connected to the steering wire and control wire.

In yet another embodiment, an intravascular device delivery system includes an elongated member, a steering wire, a control wire, a distal end cap, and a handle. The elongate member includes a body, a central lumen, a steering lumen, and a control lumen. The body has a proximal end and a distal end at opposing ends of the body, and an outer surface and an inner surface defining a wall therebetween. The inner surface defines the central lumen, which extends in a longitudinal direction. The steering lumen is defined by a steering lumen surface located in the wall. The steering lumen surface has a steering lumen lining, which defines a steering lumen diameter. The control lumen is defined by a control lumen surface located in the wall. The control lumen surface has a control lumen lining, which defines a control lumen diameter. The steering wire is located in the steering lumen and the control wire is located in the control lumen. The distal end cap is positioned at the distal end of the body. The distal end cap has a steering aperture and a control aperture. The steering aperture is rotationally aligned with the steering lumen and the control aperture is rotationally aligned with the control lumen. The steering wire has a distal end piece located at a distal end of the steering wire and distally of the distal end of the steering lumen. The handle is connected to the proximal end of the body and operably connected to the steering wire and control wire.

This summary is provided to introduce a selection of concepts that are further described below in the detailed description. This summary is not intended to identify specific features of the claimed subject matter, nor is it intended to be used as an aid in limiting the scope of the claimed subject matter.

Additional features of embodiments of the disclosure will be set forth in the description which follows. The features of such embodiments may be realized by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which.

DETAILED DESCRIPTION

Figure 1:
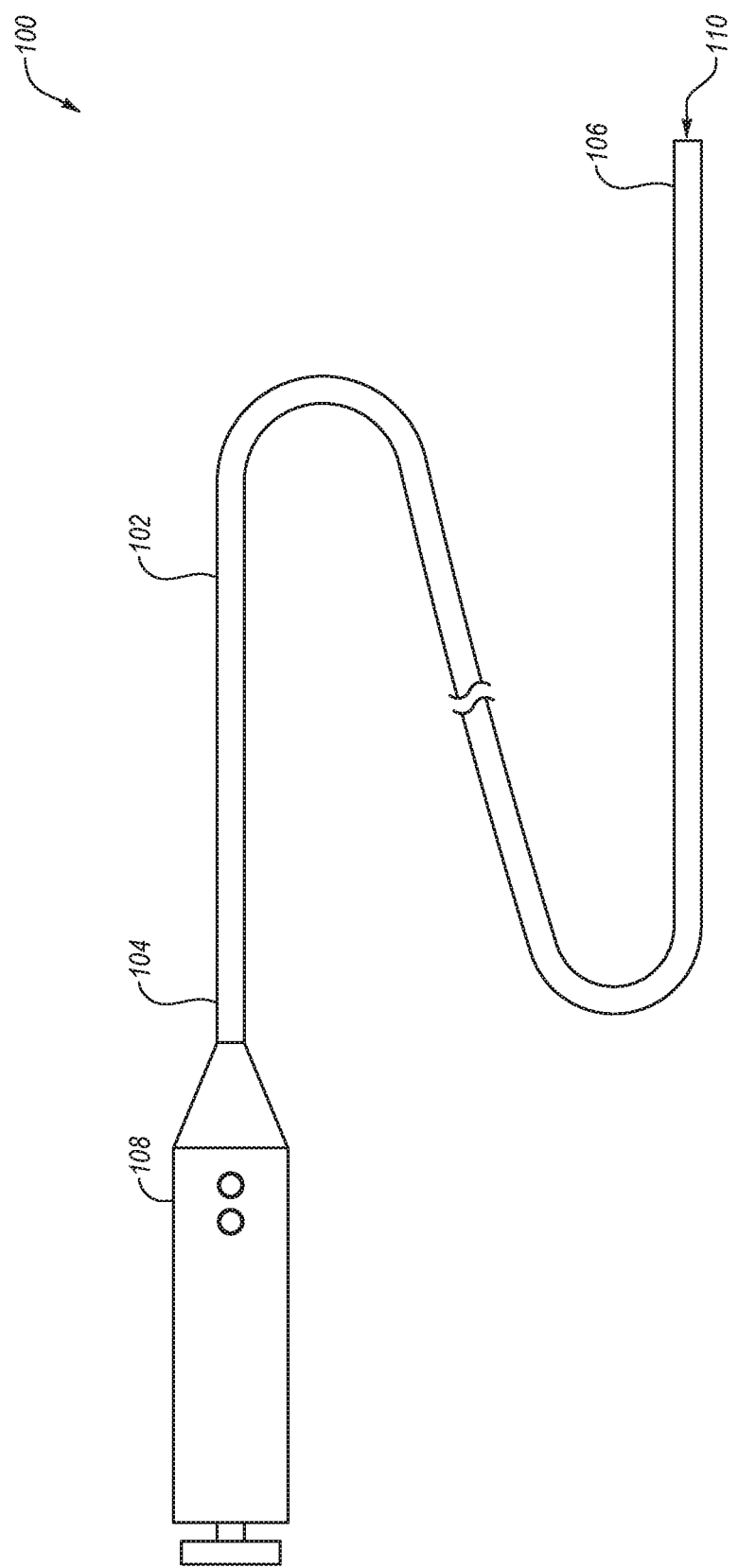
FIG. 1 is a schematic representation of an embodiment of an intravascular device delivery system, according to the present disclosure.

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to manufacturing and using intravascular device delivery systems or other steerable intravascular system. An intravascular device delivery system may allow a medical professional to deliver an intravascular or other medical device to a target location in a patient's body. While the present disclosure will describe intravascular device delivery systems and applications thereof in relation to intravascular procedures in the heart, it should be understood that the devices, systems, and methods described herein may be applicable to other bodily lumens and/or cavities. Additionally, elements described in relation to any embodiment depicted and/or described herein may be combinable with elements described in relation to any other embodiment depicted and/or described herein. For example, any element described in relation to an embodiment depicted in FIG. 2 may be combinable with any element of an embodiment described in FIG. 4, and any element described in relation to an embodiment described in FIG. 6 may be combinable with any element of an embodiment depicted in FIG. 3.

An intravascular device delivery system may include a flexible elongated member that has a distal end and a proximal end. A handle may be connected to a proximal end of the elongated member to allow a user, such as a medical professional and/or clinician, to control one or more movements of the elongated member. An intravascular device may be positioned at and/or connected to the distal end of the elongated member.

In some embodiments, the elongated member may include a plurality of elements. For example, the elongated member may include a plurality of elements that extend from the proximal end to the distal end. In some embodiments, at least one of the elements of the elongated member may include a plurality of lumens therethrough to allow steerability of the element. In at least one embodiment, at least one element of the elongated member may be steerable in at least two planes.

In some embodiments, the handle may include one or more controls (e.g., a knob, a button, a lever, or other controls) that may move at least one part of the intravascular device delivery system relative to another. For example, the handle may include one or more controls for moving at least one element of the elongated member relative to another element of the elongated member. The handle may move an inner element relative to an outer element of the elongated member in a proximal direction, in a distal direction, in a rotational direction, or combinations thereof.

FIG. 1 illustrates a schematic representation of an intravascular device delivery system 100. The system 100 may include an elongated member 102 having a proximal end 104 and a distal end 106. A handle body 108 may be connected to the proximal end 104 of the elongated member 102. An intravascular device 110 may be positioned at and/or connected to the distal end 106.

The elongated member 102 may be flexible, allowing the elongated member 102 to traverse a patient's tortuous vasculature or other anatomy. In some embodiments, the elongated member 102 may deliver the intravascular device 110 (not visible) to a target location in the patient's body, such as delivering a heart valve repair device to the heart. In other embodiments, the system 100 and elongated member 102 may be provided without an intravascular device 110 at the distal end 106 such that the system may recapture, reposition, or otherwise move an intravascular device previously positioned in the patient's body.

The elongated member 102 of the system 100 may include one or more elements therein. An element of the elongated member 102 may include a catheter, a guidewire, a sheath, a drive cable, other tubular and/or solid elements, or combinations thereof. In some embodiments an element of the elongated member 102 may extend the entire length of the elongated member 102 from a proximal end 104 to a distal end 106 of the elongated member 102. In other embodiments, an element of the elongated member 102 may have a length less than the entire length of the elongated member 102. For example, an element may provide support to the elongated member 102 from the proximal end 104 toward the distal end 106 without continuing the entire length to the distal end 106.

Figure 2:
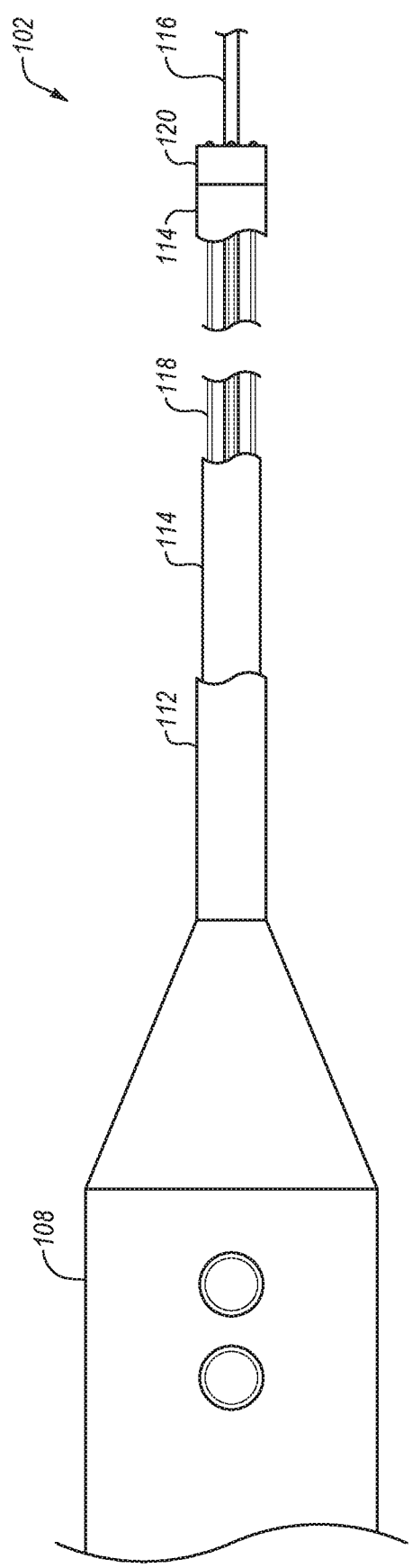
FIG. 2 is a side partial cutaway view illustrating an embodiment of the steering cables of the intravascular device delivery system of FIG. 1, according to the present disclosure.

FIG. 2 is a side partial cutaway view of part of an embodiment of the elongated member 102 of the intravascular device delivery system 100 of FIG. 1. FIG. 2 illustrates the elongated member 102 connected to the handle body 108. In some embodiments, the elongated member 102 may include an outer sheath 112, a delivery catheter 114, and an inner catheter 116. In the depicted embodiment, the delivery catheter 114 is a steerable catheter having one or more steering wires or cables 118 extending through at least a portion of the length of the delivery catheter 114 to a distal end cap 120 of the elongated member 102. While the delivery catheter 114 illustrated in FIG. 2 is a steerable catheter, one or more of the other elements of the elongated member 102 may be steerable in addition to or in alternative to the delivery catheter 114. For example, the inner catheter 116 may be steerable in at least one plane and the delivery catheter 114 may be steerable in at least one plane. In other examples, the inner catheter 116 may be steerable and the delivery catheter 114 may not be steerable.

The one or more steering cables 118 may be connected to the handle body 108. The handle body 108 may include one or more controls to move, tension, or otherwise actuate at least one of the steering cables 118. In one embodiment steering cable 118 may be a single wire. Alternatively, in order to have increased flexibility but still have sufficient strength, steering cable 118 is a cable comprising multiple single wires. It will be appreciated that steering cable 118 may comprise various numbers of single wires. In one embodiment, steering cable 118 comprise 133 single wires (7×19). In another embodiment, the multiple single wires in steering cable 118 may be wound together in various patterns know in the art to provide additional strength.

In some embodiments, the steering cables 118 may be a wire or plurality of wires including or made of tungsten, steel, titanium alloy, aluminum alloy, nickel alloy, other metals, a shape memory material (such as a shape memory alloy or shape memory polymer), inorganic polymer, organic polymer, glasses, ceramics, carbon materials, or other flexible material with sufficient tensile strength. For example, at least one of the steering cables 118 may be a braided steel cable. In another example, at least one of the steering wires may be an extruded polymer strand. In yet another example, at least one of the steering wires may be a polymer core with metal wires braided around the core.

In some embodiments, a steering cable 118 may have a tensile strength in a range having an upper value, a lower value, or an upper and lower value including any of 12 pounds, 15 pounds, 20 pounds, 25 pounds, 30 pounds, 40 pounds, 50 pounds, 60 pounds, 70 pounds, 80 pounds, 90 pounds, 100 pounds, or any values therebetween. For example, a steering cable 118 may have a tensile strength greater than 12 pounds. In other examples, a steering cable 118 may have a tensile strength less than 100 pounds. In yet other examples, a steering cable 118 may have a tensile strength in a range of 12 pounds to 100 pounds. In further examples, a steering cable 118 may have a tensile strength in a range of 20 pounds to 80 pounds. In at least one example, a steering cable 118 may have a tensile strength greater than 40 pounds.

At least one of the steering cables 118 may be connected to a distal end cap 120 located at or near the distal end (such as distal end 110 shown in FIG. 1) of the elongated member 102. The distal end cap 120 may abut the delivery catheter 114 (or other steerable element of the elongated member 102). In some embodiments, at least a part of the one of the steering cables 118 is longitudinally fixed relative to the distal end cap 120. The distal end cap 120 may have one or more apertures in a longitudinal direction therethrough to receive the steering cables 118.

In some embodiments, the elongated member 102 may be steerable by applying a tension force to a steering cable 118 of the delivery catheter 114. The tension force may be transmitted through the steering cable 118 from a proximal end to a distal end. For example, the tension force may be applied by or at the handle body 108 and transmitted through the steering cable 118 to the distal end cap 120 at the distal end of the delivery catheter 114. In other embodiments, the tension force may be applied at a location intermediate of the proximal end and the distal end of the elongated member 102. The tension force of along the steering cable 118 may be radially displaced from a longitudinal axis of the delivery catheter 114, and the radial displacement may result in a torque being applied to the delivery catheter 114 by the tension force. The torque may deflect at least a portion of the delivery catheter 114.

In some embodiments, the deflected portion of the delivery catheter 114 may be selected by varying one or more properties of the delivery catheter 114 at the desired deflection location. For example, the delivery catheter 114 may have one or more relief cuts made in the in the delivery catheter 114 to increase the flexibility of the delivery catheter 114 in the region of the relief cuts. The weakened portion of the delivery catheter 114 may preferentially flex (e.g., flex prior to and/or flex more than other, non-weakened portions of the delivery catheter 114 when tension is applied to the steering cable 118). In other examples, the delivery catheter 114 may include a material with a varying durometer along a length thereof. The varying durometer may provide a delivery catheter 114 with one or more regions that are less rigid than other portions of the delivery catheter 114. A region of the delivery catheter 114 with a lower durometer may preferentially flex relative to a region with higher durometer. In yet other embodiments, a stiffness of the delivery catheter 114 may vary along a length thereof due at least partially to variations in a reinforcement layer, as will be described more in relation to FIG. 4.

Figure 3:
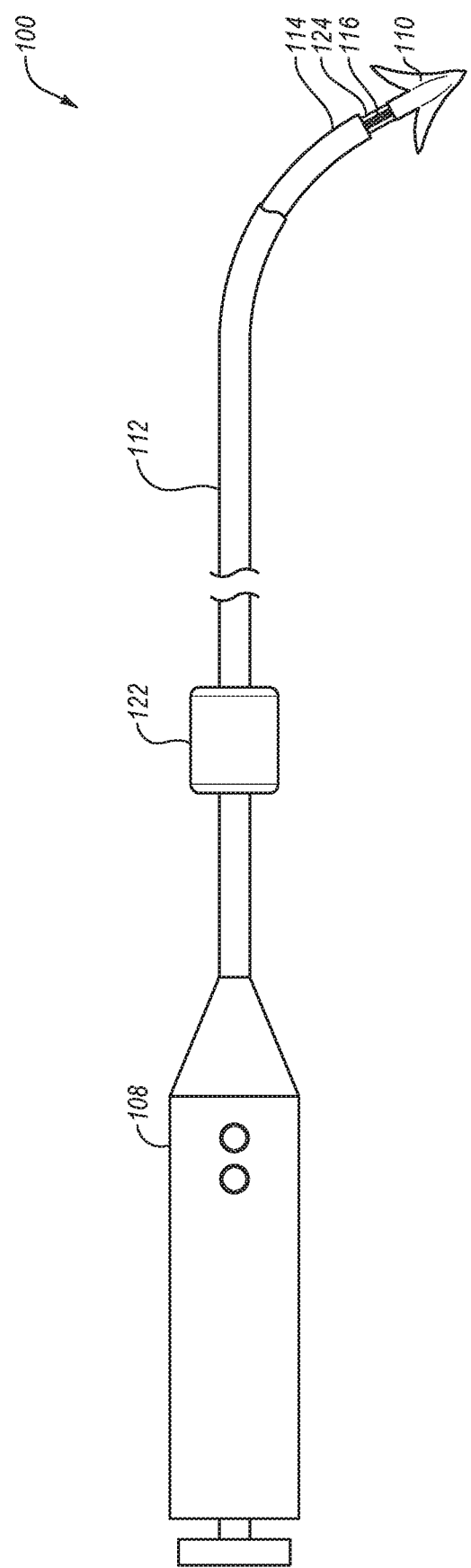
FIG. 3 is a side partial cutaway view illustrating an embodiment of the control wires and the intravascular device of FIG. 1, according to the present disclosure.

FIG. 3 illustrates an embodiment of the intravascular device delivery system 100 with one or more control wires 124 located in the delivery catheter 114. In some embodiments, a control member 122 may be located distally of the handle body 108. In other embodiments, the control member 122 may be part of the handle body 108. The control member 122 may be operably connected to the one or more control wires 124 and may allow a user to apply a tension force to the control wires 124. In some examples, control wire 124 comprises a suture. In some embodiments, one or more of the control wires 124 may be tensioned while a portion of the elongated member 102 is deflected, such as by tension applied to a steering cable 118 described in relation to FIG. 2. The tension force or forces applied to the control wires 124 may alter the position of at least part of the elongated member 102. In one embodiment control wire 124 may extend through the delivery catheter 114 from the control member 122 to the intravascular device 110. In this embodiment, control wire 124 is used to control at least a portion of the intravascular device 110.

In some embodiments, tension force may be selectively applied to one or more of the control wires 124 at a time. In other embodiments, various tension forces may be applied to all of the control wires 124 simultaneously. In yet other embodiments, a uniform amount of tension force may be applied to all of the control wires 124 simultaneously.

At least one of the control wires 124 may extend through the delivery catheter 114 from the control member 122 to the intravascular device 110. In other embodiments, at least one of the control wires 124 may extend through the delivery catheter 114 from the handle body 108 to the intravascular device 110. For example, the control wire 124 may be connected to the intravascular device 110. In some embodiments, the control wire 124 may be connected to a movable portion of the intravascular device 110 and configured to move the movable portion when a tension force is applied to the control wire 124. In other embodiments, the control wires 124 may move at least a portion of the intravascular device 110 proximally toward the handle body 108. In at least one embodiment, the control wires 124 may be used to load at least part of the intravascular device 110 within the elongated member 102.

While control wires 124 are described herein, it should be understood that the control wires 124 may be a wire or plurality of wires including or made of steel, titanium alloy, aluminum alloy, nickel alloy, other metals, a shape memory material (such as a shape memory alloy or shape memory polymer), inorganic polymer, organic polymer, ceramic, carbon materials, or other flexible material with sufficient tensile strength. For example, a control wire 124 may be a steel cable. In another example, a control wire 124 may be a monofilament suture. In another example, a control wire 124 may be a multifilament suture. In yet another example, a control wire 124 may be a braided suture.

Figure 4:
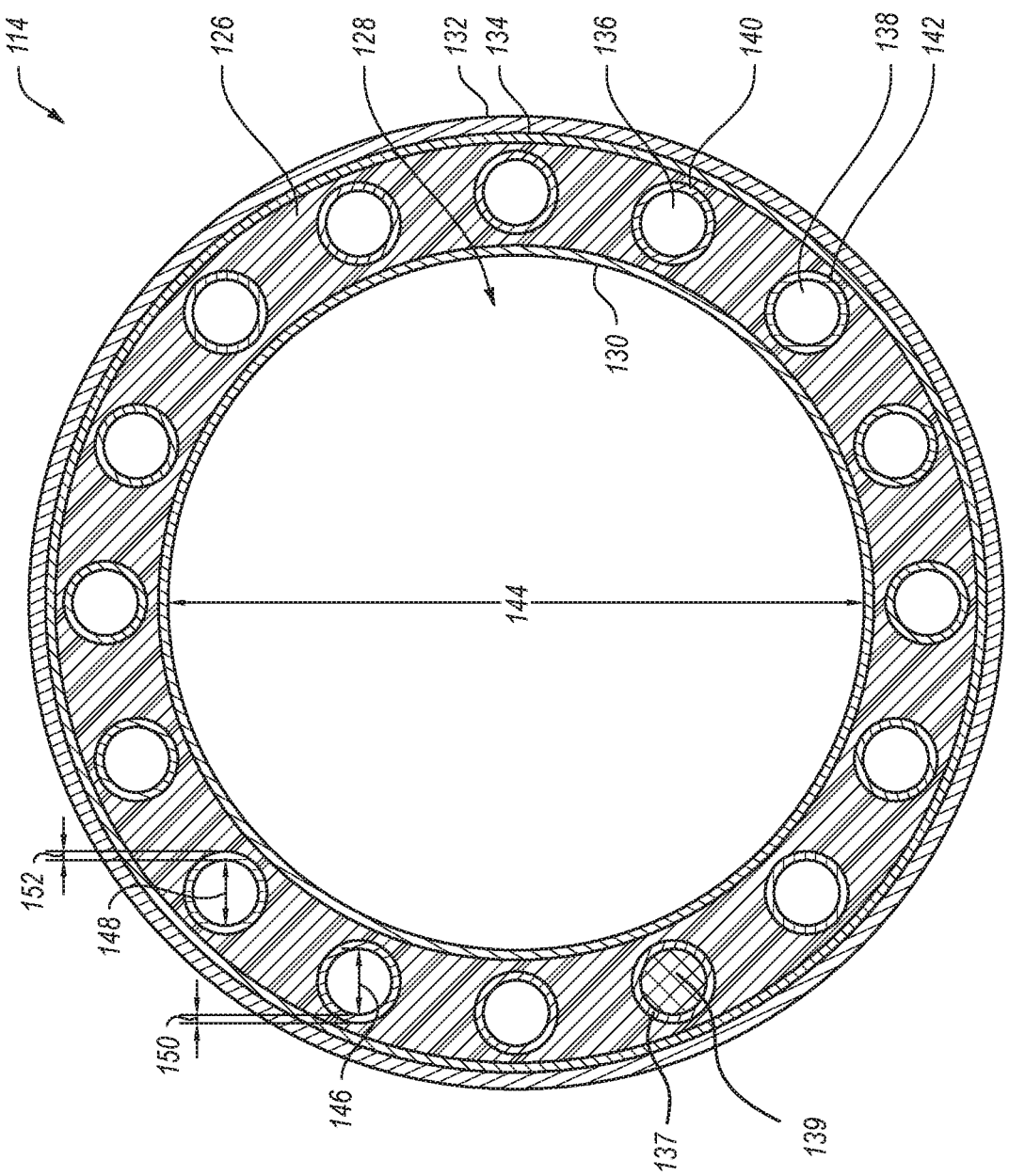
FIG. 4 is a transverse cross-sectional view of a multi-lumen catheter of the intravascular device delivery system of FIG. 1, according to the present disclosure.

FIG. 4 is a transverse cross-section of the multi-lumen delivery catheter 114, according to the present disclosure. It should be understood that while the multi-lumen catheter described herein is shown as a delivery catheter, in other embodiments, a multi-lumen catheter according to the present disclosure may be other elements in an intravascular device delivery system or may be used in other applications other than an intravascular device delivery system.

The multi-lumen delivery catheter 114 according to the present disclosure may have a body 126 made of or including a flexible material. The body 126 may be made of or include a variety of flexible body materials such as thermoplastic elastomers (TPE). In some embodiments, the body 126 may be a polyether block amide (PEBA or PEBAX). The body 126 may have a constant durometer or may have varying durometer along the longitudinal length of the body 126. For example, the body 126 may be made of or include a body material having a durometer of 25D to 75D. In another example, the body 126 may be made of or include a body material that has a durometer of about 45D. In at least one embodiment, the body material may include PEBAX 4533. In at least another embodiment, the body material may include PEBAX 3533.

The multi-lumen delivery catheter 114 has a central lumen 128. The central lumen 128 may allow passage of one or more elements of the elongated member therethrough. In other embodiments, the central lumen 128 may allow delivery of an intravascular device or implant. In yet other embodiments, the central lumen may allow fluid communication through a portion of the multi-lumen delivery catheter 114.

The central lumen 128 may have a central lumen lining 130 on an inner surface thereof. In some embodiments, the central lumen lining 130 may be a protective material that protects the body 126 from damage due to another element of the elongated member moving through or within the central lumen 128. In other embodiments, the central lumen lining 130 may be a lubricious coating that reduces friction between the body 126 and another element of the elongated member moving through or within the central lumen 128. The central lumen lining 130 may include PEBA, polytetrafluoroethylene ("PTFE"), polyetheretherketone ("PEEK"), other polymers, thermoplastic polyurethane ("TPU"), polyethylene with pebble stone surface, silicone oil stainless steel, Nitinol, other metals, or combinations thereof. In at least one embodiment, the central lumen lining 130 may include a plurality of PEBA materials having different durometers.

In some embodiments, the central lumen lining 130 may have a thickness in a range having an upper value, a lower value, or upper and lower values including any of 0.001 inches, 0.002 inches, 0.003 inches, 0.004 inches, 0.005 inches, 0.006 inches, 0.007 inches, 0.008 inches, 0.009 inches, 0.010 inches, or any values therebetween. For example, the central lumen lining thickness may be greater than 0.001 inches. In another example, the central lumen lining thickness may be less than 0.010 inches. In other examples, the central lumen lining thickness may be between 0.001 inches and 0.010 inches. In yet other examples, the central lumen lining thickness may be between 0.002 inches and 0.008 inches. In at least one example, the central lumen lining thickness may be between 0.003 inches and 0.005 inches.

In other embodiments, the multi-lumen delivery catheter 114 may have an outer lining. For example, the outer lining may be a single layer or a plurality of layers. FIG. 4 illustrates a multi-lumen delivery catheter 114 with an outer jacket 132 and a reinforcement layer 134.

In some embodiments, the outer jacket 132 may be made of or include a single material or may be made of or include different materials to impart different handling characteristics on the multi-lumen delivery catheter 114. For example, the outer jacket 132 may be made of or include softer materials to promote flexibility of the multi-lumen delivery catheter 114. In other examples, the outer jacket 132 may be made of or include stiffer materials to promote pushability and/or torqueability of the multi-lumen delivery catheter 114. In yet other examples, the outer jacket 132 may be made of or include lubricious materials to reduce friction between the multi-lumen delivery catheter 114 and the body lumen of the patient. The outer jacket 132 may include PEBA, polytetrafluoroethylene ("PTFE"), polyetheretherketone ("PEEK"), other polymers, thermoplastic polyurethane ("TPU"), polyethylene with pebble stone surface, silicone oil stainless steel, Nitinol, other metals, or combinations thereof. In at least one embodiment, the outer jacket 132 may include a plurality of PEBA materials having different durometers.

In some embodiments, the outer jacket 132 may include a radiopaque marker to improve visualization of the multi-lumen delivery catheter 114 during a medical procedure. For example, the outer jacket 132 may include a barium sulfate ($BaSO_4$), gold, platinum, platinum iridium, iodine, other radiopaque materials, or combinations thereof in a distal portion of the outer jacket 132. In at least one embodiment, the radiopaque marker may be longitudinally located in a distal and/or intermediate portion of the multi-lumen delivery catheter 114.

In some embodiments, the reinforcement layer 134 may be made of or include a material with a higher durometer than the body material, thereby providing structural support and/or protection to the body 126 of the multi-lumen delivery catheter 114. For example, the reinforcement layer 134 may include one or more layers of material. In other examples, the reinforcement layer 134 may include two layers of material containing threads that extend helically about the body 126. In other embodiments, the reinforcement layer 134 may include threads that extend about the body 126 in the transverse plane. In yet other embodiments, the reinforcement layer 134 may include threads that extend parallel to the direction of the body 126.

In some embodiments, the reinforcement layer 134 may include a plurality of threads that are woven together to provide one or more layers. For example, a layer may include a plurality of threads that extend at an angle to one another and are woven together in a repeating pattern. The plurality of threads may be woven in a diamond two wire two-under-two, over-two pattern; a half-load single wire over-one, one-under pattern; a full-load single wire over-two, under-two pattern; other alternating woven patterns; or combinations thereof. In other embodiments, the reinforcement layer may include a single thread routed substantially straight longitudinally through the plurality of threads.

The threads may be round threads, elliptical threads, or flat threads, or threads having other geometric shapes, or any combination thereof. The threads may be made of or include a variety of reinforcement materials, such as, metals, metal alloys, thermoplastics, other polymers, or combinations thereof. In some embodiments, the reinforcement material or materials may have a greater elastic modulus than the body material. For example, the reinforcement layer 134 may include a mixture of threads with different properties, such as stainless steel threads woven with polymer threads. In at least one embodiment, the reinforcement layer 134 may include a plurality of 304 stainless steel wires woven in a diamond pattern. Such an embodiment of the reinforcement layer 134 may include between 16 and 32 threads of stainless steel.

In various embodiments, the reinforcement layer 134 may reinforce different longitudinal portions of the multi-lumen delivery catheter 114. For example, the reinforcement layer 134 may extend circumferentially about the body 126 to reinforce longitudinal section(s) of the multi-lumen delivery catheter 114 in a proximal portion of the multi-lumen delivery catheter 114, an intermediate portion of the multi-lumen delivery catheter 114, a distal portion of the multi-lumen delivery catheter 114, or combinations thereof. The reinforcement layer 134 may, thereby, provide torsional, lateral, or longitudinal strengthening of the multi-lumen delivery catheter 114 in different locations to control where the multi-lumen delivery catheter 114 preferentially bends while steering and to improve navigation of the multi-lumen delivery catheter 114 through a patient's vasculature or other body lumens.

The multi-lumen delivery catheter 114 includes at least one steering lumen 136 and at least one control lumen 138. The steering lumen 136 may house a steering cable, such as the steering cables 118 described in relation to FIG. 2. The control lumen 138 may house a control wire, such as the control wires 124 described in relation to FIG. 3. In some embodiments, the multi-lumen delivery catheter 114 may include a plurality of steering lumens 136 to enable steering of the multi-lumen delivery catheter 114 in one or more planes. For example, the multi-lumen delivery catheter 114 may include 1, 2, 3, 4, 5, 6, 7, 8, or more steering lumens 136. In some embodiments, a multi-lumen delivery catheter 114 with a plurality of steering lumens 136 may have at least two steering lumen positioned at 180° intervals about the multi-lumen delivery catheter 114 to provide opposing steering within a plane. In another embodiment, a multi-lumen delivery catheter 114 with a plurality of steering lumens 136 may have at least two steering lumens 136 at less than 180° intervals, such as 90° or 120° intervals to provide steering in multiple planes.

In one embodiment, the multi-lumen delivery catheter 114 may also include at least one lumen 137 that extends from the distal end to the proximal end of the multi-lumen catheter 114. Lumen 137 may optionally have a sensor or transducer 139 disposed therein to take specified measurements. These measurements may be active or passive measurements. In some embodiments, lumen 137 may have a sensor, transducer or other device disposed therein capable of taking various types of measurements while the catheter 114 is being used. Such measurements may include fluid or air pressure, temperature, stress, strain, displacement, angular rotation, load, fluid flow or other types of characteristics of the environment. In another embodiment, the lumen may remain empty unless a removable sensor, transmitter or other device is placed into the lumen such as a pressure wire or fractional flow reserve (FFR) wire. In another embodiment, the lumen may be used to measure the pressure of the fluid communication between the distal end and the proximal end of the multi-lumen delivery catheter 114. It will be appreciated that various other types of measurements could be taken.

In some embodiments, the multi-lumen delivery catheter 114 may have a plurality of control lumens 138 to convey control wires therethrough and allow control of an intravascular device at or near the distal end of the multi-lumen delivery catheter 114 from a handle at the proximal end of the multi-lumen delivery catheter 114.

The steering cables 118 may experience up to 100 pounds of force (444.8 Newtons) during steering of some embodiments of an intravascular device delivery system. For example, larger guidewires, reinforced catheters, elongated intravascular devices, and other variants of intravascular device delivery systems may decrease lateral flexibility of one or more components of the intravascular device delivery system. One or more steering wires may be thicker than a conventional steering wire and/or may apply greater lateral force on the multi-lumen delivery catheter 114.

In some embodiments, a multi-lumen delivery catheter 114 according to the present disclosure may include one or more steering lumens 136. In some embodiments, steering lumens 136 may have with an optional steering lumen lining 140 positioned therein. A steering wire may cut laterally into a wall of a conventional lumen upon application of 100 pounds of force (444.8 Newtons) to the steering wire. The steering lumen lining 140 may be made of or include materials to protect the multi-lumen delivery catheter 114 from damage from the steering wire. In yet other examples, the steering lumen lining 140 may be made of or include lubricious materials to reduce friction between the steering wire and the surface of the steering lumen 136 and the body lumen of the patient. The steering lumen lining 140 may include PEBA, polytetrafluoroethylene ("PTFE"), polyetheretherketone ("PEEK"), other polymers, thermoplastic polyurethane ("TPU"), polyethylene with pebble stone surface, silicone oil stainless steel, Nitinol, other metals, or combinations thereof. In at least one embodiment, the steering lumen lining 140 may include a plurality of PEBA materials, PEBAX materials with Proppel to reduce friction, or other thermoplastic elastomer materials having different durometers. In other embodiments, the multi-lumen delivery catheter 114 may include or be made of PEBA, PEBAX, polytetrafluoroethylene ("PTFE"), polyetheretherketone ("PEEK"), other polymers, stainless steel, Nitinol, other metals, or combinations thereof and not include a steering lumen lining 140 therein.

The control wires may experience up to 80 pounds of force (355.9 Newtons) during steering of some embodiments of an intravascular device delivery system. For example, larger (i.e. increased longitudinal length and/or radial width) intravascular devices, more complex intravascular devices, or multiple intravascular device may increase the operational load on one or more of the control wires of the intravascular device delivery system. For example, one or more control wires may be used to draw proximally and/or radially collapse a self-expanding intravascular device, placing high loads on the control wire and, hence, on the multi-lumen delivery catheter 114.

In some embodiments, one or more of the control lumens 138 may be lined with a control lumen lining 142 positioned therein. A control cable may cut laterally into a wall of a conventional lumen upon application of 80 pounds of force (355.9 Newtons) to the control wire. The control lumen lining 142 may be made of or include materials selected to protect the multi-lumen delivery catheter 114 from damage from the control wire. In yet other examples, the control lumen lining 142 may be made of or include lubricious materials to reduce friction between the control wire and the surface of the control lumen lining 142 and the body lumen of the patient. The control lumen lining 142 may include PEBA, polytetrafluoroethylene ("PTFE"), polyetheretherketone ("PEEK"), other polymers, thermoplastic polyurethane ("TPU"), polyethylene with pebble stone surface, silicone oil stainless steel, Nitinol, other metals, or combinations thereof. In at least one embodiment, the control lumen lining 142 may include a plurality of PEBA materials having different durometers. In other embodiments, the multi-lumen delivery catheter 114 may include or be made of PEBA, polytetrafluoroethylene ("PTFE"), polyetheretherketone ("PEEK"), other polymers, stainless steel, nitinol, other metals, or combinations thereof and not include a control lumen lining 142 therein.

In some embodiments of the multi-lumen delivery catheter 114, all of the steering lumens 136 are lined by steering lumen lining 140. Alternatively, depending on the configuration of or the materials used for multi-lumen delivery catheter 114, it may be that none of the steering lumens 136 have a steering lumen lining 140. Similar various other arrangements of steering lumens 136 and steering lumen lining 140 may be utilized such as alternating lumens, every three lumens or various other arrangements for steering lumen linings 140.

Likewise, in some embodiments of the multi-lumen delivery catheter 114, all of the control lumens 138 are lined by control lumen lining 142 positioned therein. Alternatively, depending on the configuration of or the materials used for multi-lumen delivery catheter 114, it may be that none of the control lumens 138 have a control lumen lining 142. Similar various other arrangements of control lumens 138 and control lumen linings 142 may be utilized such as alternating lumens, every three lumens or various other arrangements for control lumen linings 142 in control lumens 138.

It will also be appreciated that various combinations of and arrangements of steering lumens 136, optional steering lumen linings 140, control lumens 130, and optional control lament linings 142 may be utilized. In one embodiment, every other steering lumen 136 may be lined by steering lumen lining 140. Alternatively, control lumens 138 may be lined in alternating fashion by control lumen lining 142. Various other numbers of alternating arrangements of lined lumens may be used for the steering lumen and control lumen.

The central lumen 128 has a central lumen width 144. In the depicted embodiment, the central lumen 128 has a circular cross-sectional shape and the central lumen width 144 is the diameter of the central lumen 128. In some embodiments, the central lumen 128 may have other transverse cross-sectional shapes, such as rectangular, ellipsoid, polygonal, irregular, or other shapes. In such embodiments, the central lumen width 144 may be the shortest distance between two points on opposing sides of the center of the central lumen 128.

In some embodiments, the central lumen width 144 may be in a range having upper values, lower values, or upper and lower values including any of 0.050 inches, 0.060 inches, 0.070 inches, 0.080 inches, 0.090 inches, 0.100 inches, 0.110 inches, 0.120 inches, 0.130 inches, 0.140 inches, 0.150 inches, 0.160 inches, 0.170 inches, 0.180 inches, 0.190 inches, 0.200 inches, 0.210 inches, 0.220 inches, 0.230 inches, 0.240 inches, 0.250 inches, 0.260 inches, 0.270 inches, 0.280 inches, 0.290 inches, 0.300 inches, 0.310 inches, 0.320 inches, 0.330 inches, 0.340 inches, 0.350 inches, 0.360 inches, 0.370 inches, 0.380 inches, 0.390 inches, 0.400 inches, or any values therebetween. For example, the central lumen width 144 may be greater than 0.050 inches. In other examples, the central lumen width 144 may be less than 0.400 inches. In yet other examples, the central lumen width 144 may be in a range of 0.050 inches to 0.400 inches. In further examples, the central lumen width 144 may be in a range of 0.200 inches to 0.300 inches. In at least one example, the central lumen width 144 may be about 0.255 inches. In other embodiments, the central lumen width 144 may be greater than 0.400 inches.

In the illustrated embodiment of a multi-lumen delivery catheter 114 of FIG. 4, a plurality of steering lumens 136 may be positioned substantially opposing one another across the central lumen 128. In other embodiments, a plurality of steering lumens 136 may be positioned elsewhere in the body 126 of the multi-lumen delivery catheter 114. A steering lumen 136 may have a steering lumen width 146. In the depicted embodiment, the steering lumens 136 are circular in cross section and the steering lumen width 146 is the diameter of a steering lumen 136. In other embodiments, the steering lumen 136 may have other transverse cross-sectional shapes, such as rectangular, ellipsoid, polygonal, irregular, or other shapes. In such embodiments, the steering lumen width 146 may be the shortest distance between two points on opposing sides of the center of the steering lumen 136. It will be appreciated that in other embodiments of a multi-lumen delivery catheter having a plurality of steering lumens 136, steering lumens 136 may have a variety of cross-sectional shapes in the same multi-lumen delivery catheter.

In some embodiments, the steering lumen width 146 may be in a range having upper values, lower values, or upper and lower values including any of 0.005 inches, 0.006 inches, 0.007 inches, 0.008 inches, 0.009 inches, 0.010 inches, 0.011 inches, 0.012 inches, 0.013 inches, 0.014 inches, 0.015 inches, 0.016 inches, 0.017 inches, 0.018 inches, 0.019 inches, 0.020 inches, 0.021 inches, 0.022 inches, 0.023 inches, 0.024 inches, 0.025 inches, 0.026 inches, 0.027 inches, 0.028 inches, 0.029 inches, 0.030 inches, 0.031 inches, 0.032 inches, 0.033 inches, 0.034 inches, 0.035 inches, 0.036 inches, 0.037 inches, 0.038 inches, 0.039 inches, 0.040 inches, or any values therebetween. For example, the steering lumen width 146 may be greater than 0.005 inches. In other examples, the steering lumen width 146 may be less than 0.040 inches. In yet other examples, the steering lumen width 146 may be in a range of 0.005 inches to 0.040 inches. In further examples, the steering lumen width 146 may be in a range of 0.010 inches to 0.030 inches. In at least one example, the steering lumen width 146 may be about 0.022 inches. In other embodiments, depending upon the application, the steering lumen width 146 may be in a range of 0.003 to 0.040 inches.

In the illustrated embodiment of a multi-lumen delivery catheter 114 of FIG. 4, a plurality of control lumens 138 may be positioned substantially opposing one another across the central lumens 128. In other embodiments, a plurality of control lumen 138 may be positioned elsewhere in the body 126 of the multi-lumen delivery catheter 114. A control lumen 138 may have a control lumen width 148. In the depicted embodiment, the control lumen 138 are circular in cross section and the control lumen width 148 is the diameter of a control lumen 138. In other embodiments, the control lumen 138 may have other transverse cross-sectional shapes, such as rectangular, ellipsoid, polygonal, irregular, or other shapes. In such embodiments, the control lumen width 148 may be the shortest distance between two points on opposing sides of the center of the control lumen 138. It will be appreciated that in other embodiments of a multi-lumen delivery catheter 114 having a plurality of control lumens 138, control lumens 138 may have a variety of cross-sectional shapes in the same multi-lumen delivery catheter.

In some embodiments, the control lumen width 148 may be in a range having upper values, lower values, or upper and lower values including any of 0.005 inches, 0.006 inches, 0.007 inches, 0.008 inches, 0.009 inches, 0.010 inches, 0.011 inches, 0.012 inches, 0.013 inches, 0.014 inches, 0.015 inches, 0.016 inches, 0.017 inches, 0.018 inches, 0.019 inches, 0.020 inches, 0.021 inches, 0.022 inches, 0.023 inches, 0.024 inches, 0.025 inches, 0.026 inches, 0.027 inches, 0.028 inches, 0.029 inches, 0.030 inches, 0.031 inches, 0.032 inches, 0.033 inches, 0.034 inches, 0.035 inches, 0.036 inches, 0.037 inches, 0.038 inches, 0.039 inches, 0.040 inches, or any values therebetween. For example, the control lumen width 148 may be greater than 0.005 inches. In other examples, the control lumen width 148 may be less than 0.040 inches. In yet other examples, the control lumen width 148 may be in a range of 0.005 inches to 0.040 inches. In further examples, the control lumen width 148 may be in a range of 0.010 inches to 0.030 inches. In at least one example, the control lumen width 148 may be about 0.022 inches. In other embodiments, depending upon the application, the control lumen width 148 may be in a range of 0.003 to 0.040 inches.

In the depicted embodiment, the steering lumens 136 each have substantially equal steering lumen widths 146. In other embodiments, at least one of the steering lumens 136 may have a different steering lumen width 146 than another steering lumen 136. Similarly, in the depicted embodiment, the control lumens 138 each have substantially equal control lumen widths 148. In other embodiments, at least one of the control lumens 138 may have a different control lumen width 148 than another control lumen 138.

In the depicted embodiment in FIG. 4, the steering lumen width 146 and the control lumen width 148 are substantially equal. In other embodiments, the steering lumen width 146 and the control lumen width 148 may be different. For example, at least one of the steering lumen widths 146 may be greater than at least one of the control lumen widths 148. In other examples, at least one of the steering lumen widths 146 may be less than at least one of the control lumen widths 148.

The steering lumen lining 140 has a steering lumen lining thickness 150 and the control lumen lining 142 has a control lumen lining thickness 152. In some embodiments, the steering lumen lining thickness 150 may be in a range having an upper value, a lower value, or upper and lower values including any of 0.001 inches, 0.002 inches, 0.003 inches, 0.004 inches, 0.005 inches, 0.006 inches, 0.007 inches, 0.008 inches, 0.009 inches, 0.010 inches, or any values therebetween. For example, the steering lumen lining thickness 150 may be greater than 0.001 inches. In another example, the steering lumen lining thickness 150 may be less than 0.010 inches. In other examples, the steering lumen lining thickness 150 may be between 0.001 inches and 0.010 inches. In yet other examples, the steering lumen lining thickness 150 may be between 0.002 inches and 0.008 inches. In at least one example, the steering lumen lining thickness 150 may be between 0.003 inches and 0.005 inches.

In some embodiments, the control lumen lining thickness 152 may be in a range having an upper value, a lower value, or upper and lower values including any of 0.001 inches, 0.002 inches, 0.003 inches, 0.004 inches, 0.005 inches, 0.006 inches, 0.007 inches, 0.008 inches, 0.009 inches, 0.010 inches, or any values therebetween. For example, the control lumen lining thickness 152 may be greater than 0.001 inches. In another example, the control lumen lining thickness 152 may be less than 0.010 inches. In other examples, the control lumen lining thickness 152 may be between 0.001 inches and 0.010 inches. In yet other examples, the control lumen lining thickness 152 may be between 0.002 inches and 0.008 inches. In at least one example, the control lumen lining thickness 152 may be between 0.003 inches and 0.005 inches.

Figure 5:
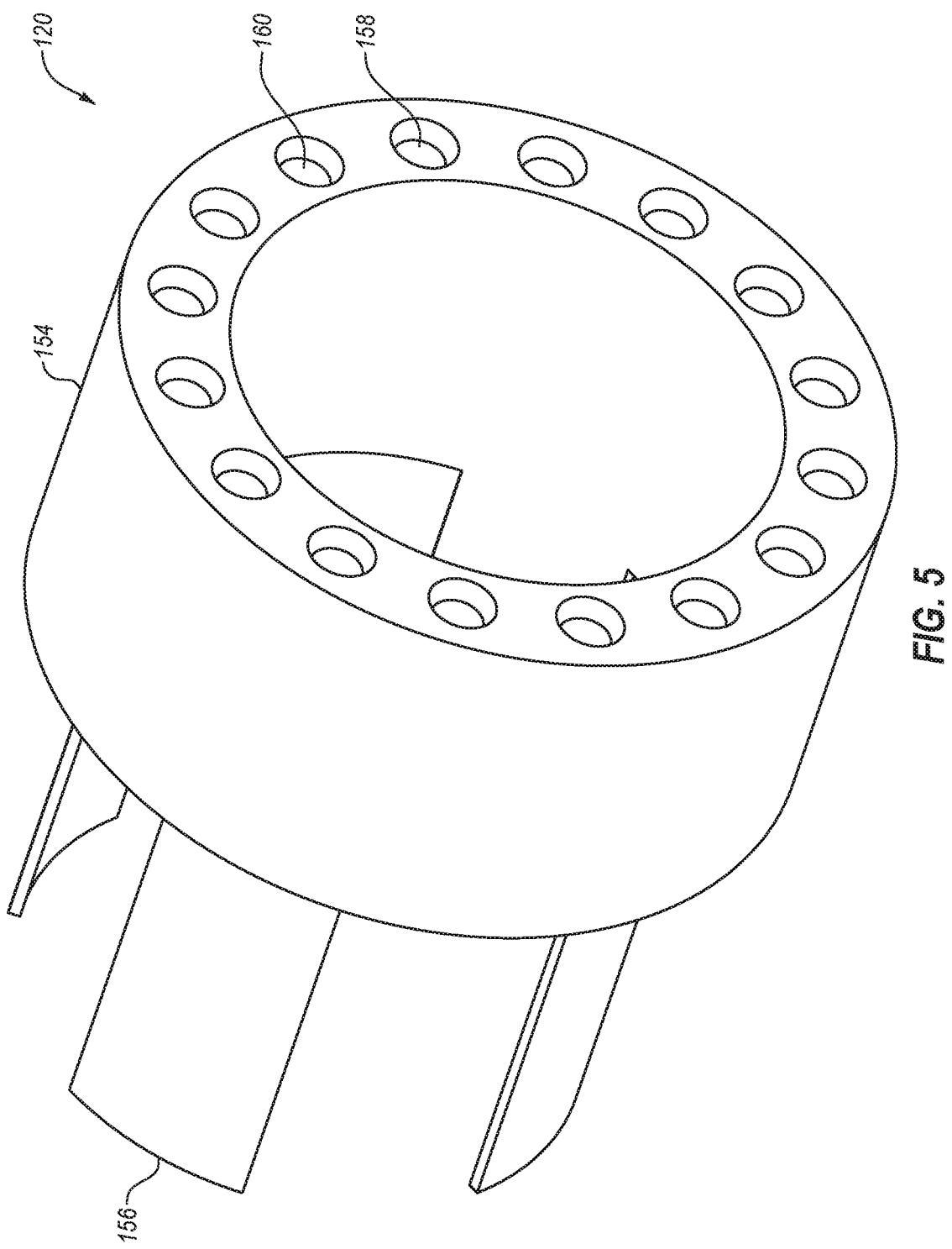
FIG. 5 is a perspective view of a distal end cap of intravascular device delivery system of FIG. 1, according to the present disclosure.

The steering wires and control wires that are directed through the multi-lumen delivery catheter may be directed through and/or anchored to a distal end cap 120, as shown in FIG. 5. The distal end cap 120 may be made of an end cap material with a higher durometer and/or elastic modulus than the body of the multi-lumen delivery catheter. In some embodiments, the distal end cap 120 may be made of or include a metal, a polymer, a ceramic, other material, or combinations thereof. For example, the distal end cap 120 may include or be made of a steel alloy, a titanium alloy, an aluminum alloy, a nickel alloy, or other metals.

In some embodiments, the distal end cap 120 may have a ring body 154 through which a plurality of apertures may extend in a longitudinal direction. One or more arms 156 may be connected to the ring body 154 on a proximal side of the ring body 154. In some embodiments, one or more arms 156 may be connected to the ring body 154 by a mechanical fastener (e.g., a screw, a pin, a clip, a tie, a rod, etc.), an adhesive, a friction fit, a snap fit, a compression fit, or combinations thereof. For example, an arm 156 may be connected to the ring body 154 by a snap fit reinforced with a screw. In other examples, an arm 156 may be connected to the ring body 154 by an adhesive, such as a cyanoacrylate, and a cross-pin.

In other embodiments, one or more arms 156 may be integrally formed with the ring body 154. For example, an arm 156 may be welded to the ring body 154. In other examples, an arm 156 may be monolithic with the ring body 154, such as in a distal end cap 120 in which the ring body 154 and arms 156 are cast simultaneously by such methods as injection molding, sand casting, or other casting techniques. In yet other examples, a distal end cap 120 may have the ring body 154 and arms 156 machined from a monolithic block of material, such as a metal alloy or a polymer.

In some embodiments, the arms 156 extend in a proximal direction and may be configured to fit within the central lumen of the multi-lumen delivery catheter, such as the central lumen 128 described in relation to FIG. 4. The one or more arms 156 of ring body 154 inside the central lumen 128 may provide support to the ring body 154. The one or more arms 156 may resist rotation of the distal end cap 120 relative to the multi-lumen delivery catheter 114 upon a distal force being applied to the distal end cap 120 by a tension force of the one or more steering wires.

In other embodiments, the arms 156 extend in a proximal direction and may be configured to be embedded in the wall of the multi-lumen delivery catheter. For example, a reinforcement braid inside the wall of the multi-lumen delivery catheter may terminate proximally of the distal end of the multi-lumen delivery catheter in order to provide longitudinally and/or radial space for the arms 156.

The plurality of apertures in the ring body 154 include at least one control aperture 158 and at least one steering aperture 160. In some embodiments, the steering apertures 160 may be sized and positioned to align with the steering lumen of a multi-lumen delivery catheter. For example, the steering apertures 160 may have a width or diameter similar to the steering lumen width 146 described in relation to FIG. 4.

In some embodiments, the control apertures 158 may be sized and positioned to align with the steering lumen of a multi-lumen delivery catheter. For example, the steering apertures may have a width or diameter similar to the control lumen width 148 described in relation to FIG. 4.

Figure 6:
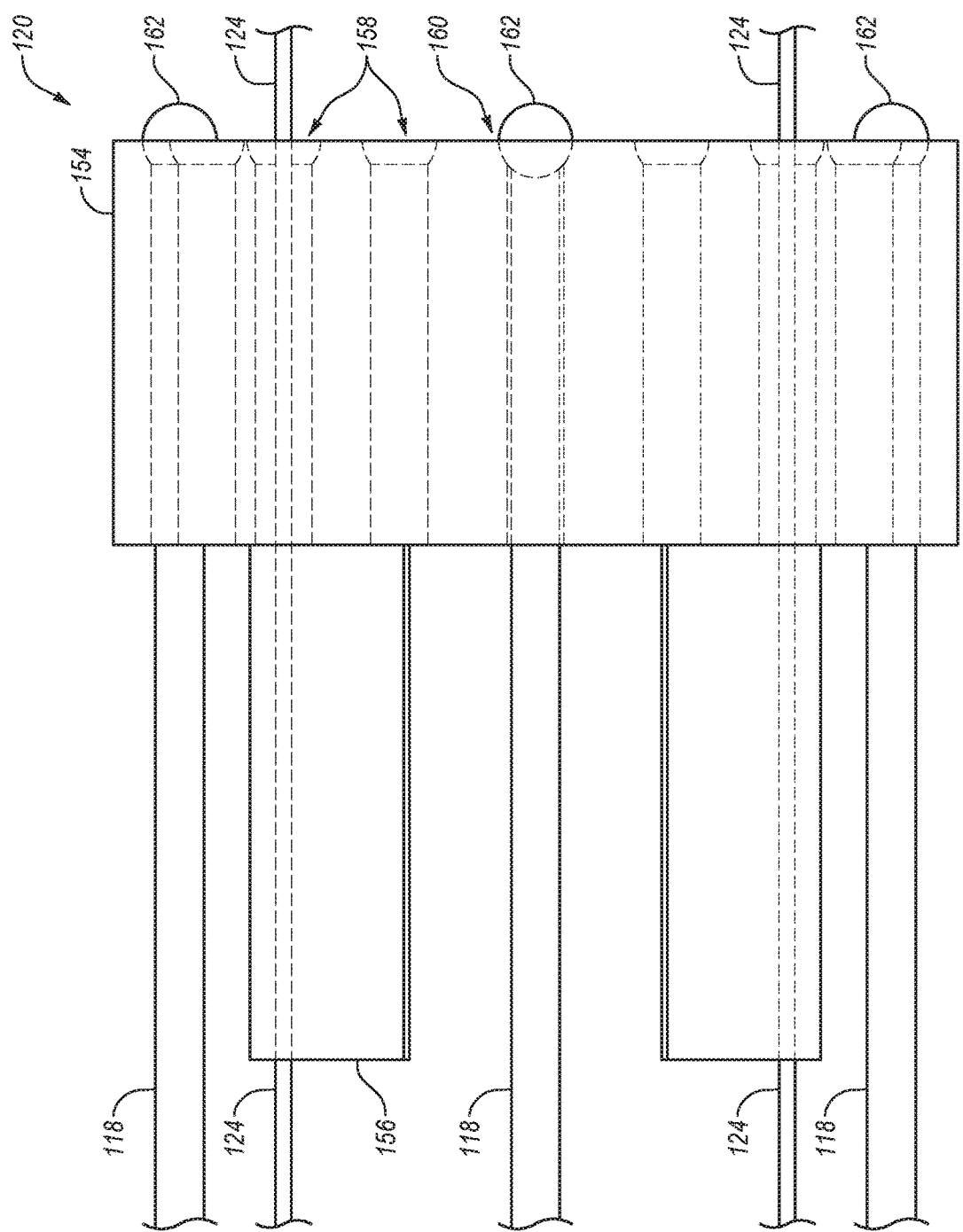
FIG. 6 is a side view of the distal end cap of FIG. 5 with steering cable and control wires therethrough, according to the present disclosure.

FIG. 6 illustrates the distal end cap 120 with an embodiment of steering cables 118 and control wires 124 extending longitudinally through the ring body 154. The arms 156 of the distal end cap 120 may be radially within the control apertures 158 and/or the steering apertures 160. In some embodiments, the control wires 124 extend through the distal end cap 120 and continue distally beyond the distal end cap 120. In other embodiments, one or more of the control wires 124 may connected to or be otherwise operably coupled to other movable elements of an intravascular device delivery system.

In some embodiments, the steering cable 118 may extend through the ring body 154 of the distal end cap 120. In other embodiments, the steering cables 118 may terminate within the ring body 154. The steering cable 118 may have a distal end piece 162. The distal end piece 162 may have a transverse dimension larger than a transverse dimension of the steering aperture 160, limiting and/or preventing the proximal movement of the distal end piece 162 relative to the ring body 154. For example, the distal end piece 162 may have a diameter greater than a diameter of the steering aperture 160. As described herein, the steering aperture 160 may have a width and/or diameter similar to the steering lumen width. The distal end piece 162 of the steering cable 118, may have a transverse dimension greater than any of 0.010 inches, 0.011 inches, 0.012 inches, 0.013 inches, 0.014 inches, 0.015 inches, 0.016 inches, 0.017 inches, 0.018 inches, 0.019 inches, 0.020 inches, 0.021 inches, 0.022 inches, 0.023 inches, 0.024 inches, 0.025 inches, 0.026 inches, 0.027 inches, 0.028 inches, 0.029 inches, 0.030 inches, or any values therebetween.

In some embodiments, the distal end piece 162 may be connected to the steering cable by a mechanical fastener (e.g., a screw, a pin, a clip, a tie, a rod, etc.), an adhesive, a friction fit, a snap fit, a compression fit, or combinations thereof. For example, the distal end piece 162 may be connected to the steering cable 118 by a compression fit reinforced with a collet. In other examples with a steering cable 118 that is a multi-threaded cable, the distal end piece 162 may be connected to the steering cable 118 by compressing the threads of the cable around a central plug or shaft with a collet, such as a threaded collet. In yet other examples, the distal end piece 162 may be connected to the steering cable 118 by an adhesive, such as a cyanoacrylate, and a clip. In yet other embodiments, the distal end piece 162 may be integrally formed with the steering cable 118. For example, the distal end piece 162 may be welded to the steering cable 118. In other examples, the distal end piece 162 may be monolithically formed with the steering cable 118, such as a compressed and widened portion of a drawn wire.

In some embodiments, the distal end cap 120 may abut the embodiment of a multi-lumen delivery catheter 114 described herein and shown in FIG. 3. The distal end piece 162 of the steering cable 118 may allow the steering cable 118 to be longitudinally fixed in at least the proximal direction relative to the distal end cap 120 and/or a multi-lumen delivery catheter 114.

Figure 7:
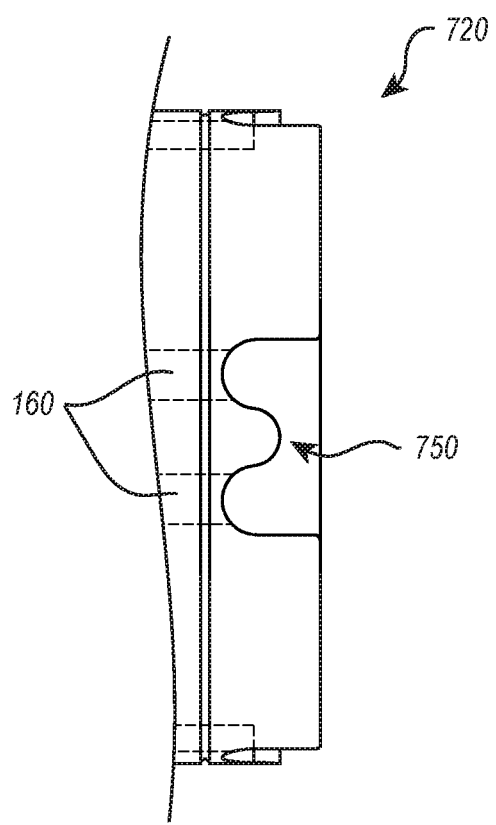
FIG. 7 is a partial cut away side view of another embodiment of a distal end cap for an intravascular device delivery system according to the present disclosure.

In another embodiment of distal end cap 120, a distal end piece such as distal end piece 162 shown in FIG. 6 is no longer needed. Rather, as illustrated in FIG. 7, distal end cap 720 includes a substantially smooth and generally "u" shaped saddle portion 750 located between a pair of steering apertures 160. Saddle portion 750 allows at least one steering cable 118 to be a continuous piece which extends distally through steering aperture 160, is looped over the saddle portion 750, and extends proximally though as second steering aperture 160 back toward the proximal end of elongated member 102 and handle body 108. The shape of saddle portion 750 allows significant tension be applied to steering cable 118 without the distal end cap 120 cutting into or deforming steering cable 118. It also allows for the force to be evenly applied while steering the multi-lumen delivery catheter 114.

In one embodiment illustrated in FIG. 7, distal end cap 720 has four saddle portions 750 and four pairs of steering apertures 160 which are symmetrically located around distal end cap 120. In other embodiments, various other numbers of and locations of saddle portions 750 and pairs of steering apertures 160 may be used. In another embodiment, saddle portions 750 and pairs of steering apertures 160 may not be symmetrically located around distal end cap 720.

As previously discussed, in some embodiments, the steering apertures 160 may be sized and positioned to align with the steering lumens 138 of a multi-lumen delivery catheter. In another embodiment, the distal end cap may include some combination of numbers (whether in pairs or not) of steering apertures 160, saddle portions 750 and distal end pieces 162 for the steering cables 118. It one embodiment, one of the steering cables 118 may be connected to the distal end of the distal end cap by distal end piece 162 as shown in FIG. 6 but other of the steering cables 118 may be continuous pieces that are looped over a saddle portion and back to the proximal end of the multi-lumen delivery catheter 114.

In at least one embodiment, an intravascular device delivery system 100, such as that described in relation to FIG. 1, including a multi-lumen delivery catheter 114 may be capable of transmitting increased steering and/or control forces relative to conventional delivery systems with an elongated member having a thinner wall than conventional delivery systems. An intravascular device delivery system 100 according to the present disclosure may, therefore, enable the use of an increased variety of intravascular devices in an increased variety of applications.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A multi-lumen catheter, the catheter comprising:
   a body having an outer surface and an inner surface defining a wall therebetween, the inner surface defining a central lumen along a longitudinal direction;
   a steering lumen defined by a steering lumen surface positioned in the wall of the body, the steering lumen surface having a steering lumen lining affixed thereto, an inner surface of the steering lumen lining defining a steering lumen width, the steering lumen lining being resistant to cutting by the steering wire;
   a control lumen defined by a control lumen surface positioned in the wall of the body, the control lumen surface having a control lumen lining affixed thereto, an inner surface of the control lumen lining defining a control lumen width, the control lumen lining being resistant to cutting by a control suture different from the steering wire; and
   an end cap disposed at a distal end of the body, the steering wire and the control suture passing through the end cap, a terminal end of the steering wire being distal a distal surface of the end cap, the control suture extending distally beyond the terminal end of the steering wire.

2. The catheter of claim 1, the catheter having a plurality of steering lumen and at least one control lumen.

3. The catheter of claim 1, further comprising a lumen extending from a distal end of the body towards a proximal end, the lumen in the wall of the body having a sensor or transducer disposed therein used to measure one of pressure, temperature, stress, strain, displacement, angular rotation, load, or fluid flow.

4. The catheter of claim 1, the steering lumen lining having a different durometer than the control lumen lining.

5. The catheter of claim 1, the steering lumen width being greater than the control lumen width.

6. The catheter of claim 1, wherein the catheter includes a plurality of control lumens and a plurality of steering lumens and the catheter includes a greater number of control lumens than steering lumens.

7. The catheter of claim 1, wherein the central lumen has a central lumen width between 0.200 inches and 0.300 inches.

8. The catheter of claim 7, wherein the steering lumen has a steering lumen width between 0.020 inches and 0.030 inches.

* * * * *